United States Patent
Holt et al.

(10) Patent No.: US 8,374,313 B2
(45) Date of Patent: Feb. 12, 2013

(54) APPARATUS AND METHODS FOR RADIATION TREATMENT OF TISSUE SURFACES

(75) Inventors: Randall W. Holt, Chico, CA (US); Steve Axelrod, Los Altos, CA (US); Robert Burnside, Mountain View, CA (US); Robert G. Neimeyer, San Jose, CA (US); Thomas W. Rusch, Hopkins, MN (US)

(73) Assignee: Xoft, Inc., Sunnyvale, CA (US)

( * ) Notice: Subject to any disclaimer, the term of this patent is extended or adjusted under 35 U.S.C. 154(b) by 425 days.

(21) Appl. No.: 12/802,744

(22) Filed: Jun. 11, 2010

(65) Prior Publication Data

US 2011/0305316 A1  Dec. 15, 2011

(51) Int. Cl.
*A61N 5/10* (2006.01)
*H05G 1/02* (2006.01)

(52) U.S. Cl. ............................ 378/65; 378/196; 378/197

(58) Field of Classification Search ................... 378/65, 378/196, 197
See application file for complete search history.

(56) References Cited

U.S. PATENT DOCUMENTS

| | | | |
|---|---|---|---|
| 4,037,110 A | | 7/1977 | Shaffer et al. |
| 5,037,374 A | * | 8/1991 | Carol ............................ 600/1 |
| 5,634,929 A | * | 6/1997 | Misko et al. ................... 606/130 |
| 5,954,647 A | * | 9/1999 | Bova et al. ..................... 600/407 |
| 6,285,735 B1 | * | 9/2001 | Sliski et al. ..................... 378/65 |
| 6,459,927 B1 | * | 10/2002 | Franklin et al. ................ 600/429 |
| 7,127,033 B2 | | 10/2006 | Lovoi et al. |
| 7,231,015 B2 | * | 6/2007 | Kumakhov ..................... 378/65 |
| 7,283,610 B2 | * | 10/2007 | Low et al. ........................ 378/65 |
| 7,796,729 B2 | * | 9/2010 | O'Brien et al. .................. 378/65 |
| 8,229,069 B2 | * | 7/2012 | Gertner et al. .................. 378/65 |
| 2009/0216062 A1 | * | 8/2009 | Axelrod et al. ................... 600/5 |
| 2009/0227827 A1 | | 9/2009 | Hausen et al. |
| 2010/0074407 A1 | | 3/2010 | Axelrod et al. |

OTHER PUBLICATIONS

Turner, John E., Atoms, *Radiation and Radiation Protection*, 1995, pp. 40-45, Second Edition, John Wiley & Sons, Inc., New York, NY, U.S.A.

* cited by examiner

*Primary Examiner* — Thomas R Artman
(74) *Attorney, Agent, or Firm* — William A. Loginov; Loginov & Associates, PLLC

(57) ABSTRACT

A device, system and method for administering radiation therapy to a tissue surface of a patient utilizes an applicator capable of controlled movement and repositioning over a selected area of tissue, under the control of a computer or controller. A servo-controlled manipulator can effect a raster scan of the desired area, such as an area of the skin, and this can be in any desired pattern such as serpentine, spiral, parallel but unidirectional, or irregular patterns. Preferably a third direction of control is included, i.e. a depth direction, with an appropriate form of depth sensor, a signal from which can be used to adjust the radiation source so that radiation of the tissue surface is consistent over varied contoured.

20 Claims, 5 Drawing Sheets

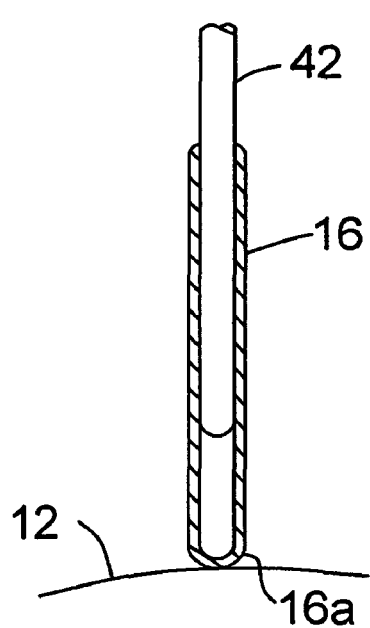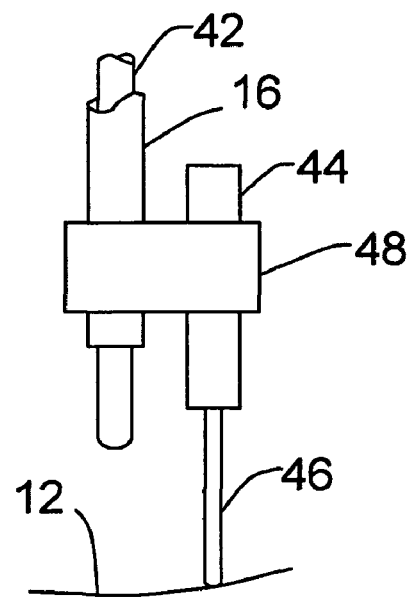
FIG. 2A  FIG. 2B
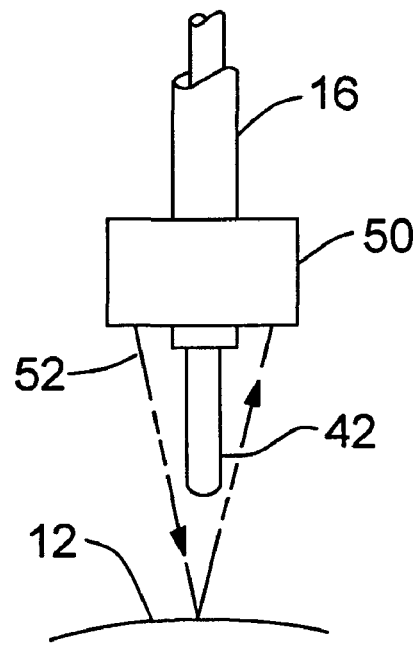
FIG. 2C

APPARATUS AND METHODS FOR RADIATION TREATMENT OF TISSUE SURFACES

BACKGROUND OF THE INVENTION

This invention relates to radiation therapy of tissue surfaces as adjuvant or primary care for proliferative disease or other pathological conditions or as primary treatment. Discussion herein is largely directed to radiotherapy of exposed anatomical surfaces, e.g. skin, for treatment of proliferative disease, but it is to be understood that the apparatus and methods may be applied to different anatomical sites whether naturally occurring or as a result of surgical intervention, and for other therapeutic purposes.

It has been demonstrated in many areas of surgical oncology that adjuvant radiation treatment following tumor resection reduces the likelihood of recurrence of cancer or other proliferative disease. The likelihood of infiltrative disease decreases with distance from a primary site in a tissue with confirmed disease.

Commonly used traditional methods of radiation surface treatment would include positioning low energy radionuclide seeds in a pattern, often on a mesh substrate, in or on a surface to be treated. Because of the low energy levels and prolonged treatment times, these seeds are often left in the patient permanently.

Traditional methods would also include large, high-energy external radiation beams in the megavolt range. Such beams are often pencil-thin and are scanned from a range of perhaps 50 to 200 cm in order to carry out a prescribed treatment. If necessary, large elements of the apparatus, or even the patient, are manipulated in order to reduce exposure of normal tissue to unnecessary levels of radiation, and to still comply with the prescription.

Recently, it has been shown that relatively low energy, high dose rate radiotherapy delivered proximate to the treatment surface can be as effective as either low dose rate seed treatment or external beam therapy. It does not require seeds be left in the patient over long periods or permanently, nor does it risk exposing normal tissue to inadvertent radiation exposure. It is therefore desirable that such techniques be made available to as great a population of patients as possible.

It is well known that radiation intensity diminishes exponentially with either attenuation resulting from materials placed between the radiation source and target, or by distance from the source, or both. Radiotherapists have therefore found that it is generally desirable to spatially separate the radiation source from the tissues being treated, or to provide an attenuating material through which the radiation must pass before encountering tissue. This reduces the intensity ratio between the radiation incident on the tissue surface and that at depth, minimizing the likelihood of over-exposing that tissue nearest the radiation source, while still delivering adequate radiation at the specified depth for effective treatment.

Early development in the application of relatively low-energy, high dose rate therapy involved development of applicators comprising relatively heavy sheets having a plurality of parallel source guides for use with radionuclide sources. These sources are often of iridium 192 positioned on wires, which are manipulated within source guides to deliver a prescribed treatment to the target tissue underlying the applicator. These surface applicators have several disadvantages, however. Their source guides have fixed spacing which may or may not be conducive to an optimal treatment plan, and further, the discrete spacing of the source guides within the applicator may contribute to non-uniformity in the delivered radiation dose. Still further, the applicator may have structural characteristics limiting its ability to conform adequately to the surface being treated without interfering with ease of source manipulation within the source guides. The so-called H.A.M. or flap applicators are representative of this sort of applicator. (Such applicators are available from Mick Radio-Nuclear Instruments, Inc., Mount Vernon, N.Y. 10550, or Nucletron, Columbia, Md.) It is an object of this invention to overcome these and other difficulties.

Emissions from iridium and other common medical isotopes usually have high-energy components which can penetrate deeply into tissue. They also emit continuously, and thus, like external-beam sources, can only be used in special, heavily-shielded rooms. In addition, concerns for the safety of personnel require isolation of the patient during treatment, shielded storage of the sources at all other times, and automated handling between the storage chamber and the applicator during patient treatment. Because of these considerations, the substantial capital expense required for such facilities dictates that treatment centers be located in urban areas so as to serve sizeable patient populations. This can result in under-serving rural patients who cannot repeatedly travel to urban treatment centers for a course of prolonged radiation treatment. Furthermore, the need for patient isolation is inconvenient for therapists, not to mention daunting for patients under treatment. Because of these limitations, it is clear that any improvements in total duration of treatment, cost, source handling and shielding requirements, patient fear factors and inconvenience would be welcome.

More recently, miniature electronic x-ray tubes have provided an alternative to use of radionuclides. Such tubes do not emit continuously; they only emit when powered in a manner causing emission and they can be turned on and off, or if desired, modulated such that their penetration depth can be controlled (by control of acceleration voltage) and their dose intensity can be controlled (by beam current) as well. One reference describing the principles and construction of such tubes is *Atoms, Radiation and Radiation Protection*, Second Edition, John E. Turner, Ph.D., CHP, 1995, John Wiley & Sons, Section 2.10. Electronic sources generally require provision for cooling, but otherwise are more versatile and convenient to use than radionuclides. They can be engineered to accommodate a wide variety of dosimetric prescription detail. Miniature x-ray tubes can be designed to emit substantially isotropically, or to emit only through a predetermined solid angle, perhaps permitting more spatially-detailed courses of treatment. Radionuclides cannot be controlled in this manner as easily. Furthermore, the x-ray energy spectrum in ranges suitable for use in this invention eliminates the need for heavily shielded structures, or "bunkers", and also permits the therapist to be in the room with the patient during therapy. Therapy can proceed in almost any medical facility, urban, rural or even mobile, and therefore, with miniature x-ray tubes, a greater population of patients can be treated, and the costs of therapy are greatly reduced. It is clear that electronic sources have already contributed significantly to making such therapy as described above more readily available and cost effective than other methods. Although the apparatus and methods of this invention may be compatible with either radionuclide or x-ray sources, it is clear that electronic x-ray sources offer many advantages as outlined above. It is a purpose of this invention to further develop those advantages.

Other objectives of the invention will become apparent from the following summary, drawings and description.

SUMMARY OF THE INVENTION

The essence of this invention is computer-driven mechanical translation, or "rastering", of a miniature x-ray radiation source of between 20 and 100 kV, but preferably around 50 kV to effectively deliver radiotherapy treatment to an area of tissue in accordance with a prescribed treatment plan. A source whose output characteristics are known may be positioned to overlie a treatment area and scanned such that the cumulative radiation delivered by the rastering conforms to the treatment prescription. The prescription may simply be uniform or may be complex in order to accommodate the case at hand. The rastering can comprise a series of sequential steps in which case the time over each target segment multiplied by the effective intensity relative to the source position is cumulated, including any contributions from adjacent dwell points. The steps can be arbitrarily spaced as finely (or even as irregularly) as one wishes, but in practice, there is little point in more divisions than necessary to deliver a result within tolerable therapeutic limits. If rather than a sequential step plan, a continuous motion plan is desired, the planning process can integrate the cumulative absorbed dose for each portion of the treatment area similarly, using source output and position, rastering speed, and source proximity as apparatus parameters.

A treatment planning protocol or program is used to establish dwell times based on iterative modeling of cumulative (or integrated) source output in order to develop a plan corresponding to the prescription. After a satisfactory plan is established which corresponds to the prescription, treatment can commence.

In one planar embodiment of the invention, the apparatus consists of an X-Y table upon which a source is mounted. The table is positioned to overlie the tissue surface to be treated, preferably such that the range of X and Y motion is adequate to encompass the target area. X and Y motions are each actuated by conventional servomotor apparatus, which in turn is driven by a computer carrying out the prescription plan.

In a non-planar case, the embodiment of the invention must accommodate the "Z" (or height) variations in the surface to maintain range between the source and treatment surface such that the desired therapeutic dose is delivered. Non-contact methods like IR ranging (Acroname, Inc., Boulder, Colo.) or laser ranging (Keyence Corporation of America, Woodcliff Lake, N.J. 07677) can be used to map the Z variations in the planning phase of the treatment, after which treatment can proceed.

If a non-contact ranging method is employed, it can also be used in real time during treatment to sense respiration or other motion of the patient as well to correct, with feedback, either range or source output to maintain the desired dose. Radiation dosimeters, for example those of MOSFET type (Best Medical Canada, Ottawa, Ontario K2K 0E4 Canada) can be positioned in the dose pattern for feedback purposes, to verify dose delivery in real time, or to signal the need for an emergency shut-down should there be a loss of control. If dosimeter shadowing detracts from effective dose delivery, the dosimeters can be positioned in pockets in a carrier sheet overlying the target area, such that the attenuation effects of the dosimeters and the sheet material are substantially uniform, and for which compensation can easily be provided. Alternatively, any of several other dosimetry methods can be used which are both conventional and known to those of skill in the art.

Contact methods of Z control can also be used as an alternative to active, automated Z control. A probe or extended catheter sheath can glide directly on the target tissue, or alternatively, a generally compliant or rigid sheet and/or drape can be placed over the treatment area upon which the source, source catheter sheath can glide to maintain Z control. A probe of an LVDT (Linear Variable Differential Transformer (Honeywell International, Inc., Columbus, Ohio) is one example of such a contact probe.

A preferred contact style probe is a catheter sheath with a preferably substantially spherical contact surface of about one (1) cm radius, with the source at the center of the spherical portion. The spherical portion glides on a fairly rigid surface overlying the target tissue to maintain Z control, hence proper range. We have discovered that an advantage of such an embodiment over prior art teaching is an unexpected increase in treatment efficiency. Where the generally spherical portion of the catheter or applicator terminus meets the contact surface, there is, in principle, only point contact so long as any surface undulations are not severe. The air gap formed around the point of contact does not significantly attenuate the radiation intensity lateral of the contact point. Prior art methods of surface treatment teach substantial, intimate contact with the target tissue rather than creating an air gap, and limitation of the direction of radiation to an area toward which the applicator is directed. Hence with this invention, the absorbed dose laterally of each contact point provides a greater contribution to the cumulative dose at each such point, thereby allowing greater spacing between dwell points, and hence faster treatment times for any target area. We have even found this increase to be sufficient to still provide a substantial improvement in absorbed dose even when the contact surface is comprised of a material which attenuates the lateral radiation. A preferred example of such a contact sheet is aluminum which also provides radiation hardening—a further advantage. A variation on this embodiment is a source catheter tip of radiation hardening nature, and a more radiation-transparent contact surface, or no overlying contact surface, where the source guide glides on or just above the target tissue.

The spherical end component preferably comprises a solid material surrounding the source, with selected attenuating (or beam hardening) characteristics. The spherical shape assures uniform attenuation in all directions, assisting in treatment planning. It also provides the option to distribute the radiation non-symmetrically in a desired way. In one direction beam attenuation or full shielding could be provided, and in other directions, for example, less attenuation or beam hardening could be provided.

Where the probe is of a non-contact type, there is no advantage to a substantially spherical contact surface to facilitate gliding along undulating target tissue or a contact sheet. In such an instance, the choice of catheter guide tip shape or design can be responsive to other priorities, for example, isodose shape, shielding, ease of sterility maintenance, operating room environment, or other attributes.

Another advantage with this invention is that, where target surfaces are not severely undulating and where Z control is responsive to the surface or can be preprogrammed as a function of X,Y positioning, many three dimensional cases can be managed by two dimensional (X,Y) rastering methods, providing a great advantage in the planning process and in time required in the operating room.

Properly instrumented, any of the Z ranging methods described above can also be used in real time during therapy for dose verification and/or safety shut-off purposes.

The apparatus and methods described above incorporate an X, Y, Z coordinate system. Equally, other coordinate systems can be employed. An example is a radial R, $\theta$, $\Phi$ system, where the source is manipulated about a point. Such a system is described in greater detail below. In such a system, two angular parameters, $\theta$ and $\Phi$, an actuator length or range, R, can be manipulated in a coordinated fashion such that a treatment plan is delivered effectively. A hybrid system might also be devised where the point about which the $\theta$ and $\Phi$ parameters rotate in the radial system is manipulated. Other coordinate systems yet may be devised and are to be included within the scope of the invention.

As described above, the invention uses individual actuators to control each of many apparatus parameters. It is to be understood that many, if not all, of these control elements could be replaced by a properly programmed robot. Also, if the prescription for the case at hand is simple, variable control of some parameters or degrees of freedom of movement can be eliminated entirely without departing from the invention herein described. Such methods and opportunities would be apparent and are well known to those familiar with the robotic arts. Furthermore, although the description above assumes a miniature x-ray tube, some of the concepts are appropriate for use with radionuclide sources as well, and such use is to be considered within the scope of the invention.

By utilizing this invention, many limitations of the prior art applicators are eliminated, including dose variations resulting from inflexible treatment patterns, long treatment times, poor conformance to anatomical contours and potential source manipulation difficulties.

DESCRIPTION OF THE DRAWINGS

FIGS. 2A-E depict schematically, exemplary methods with which the surface contours of the area to be treated with the apparatus of FIG. 1 can be mapped or used to control radiation treatment.

FIG. 4 is a longitudinal cross view of the apparatus of

FIG. 3 showing control of the Φ parameter of the R, θ, Φ coordinate system.

DESCRIPTION OF PREFERRED EMBODIMENTS

Figure 1:
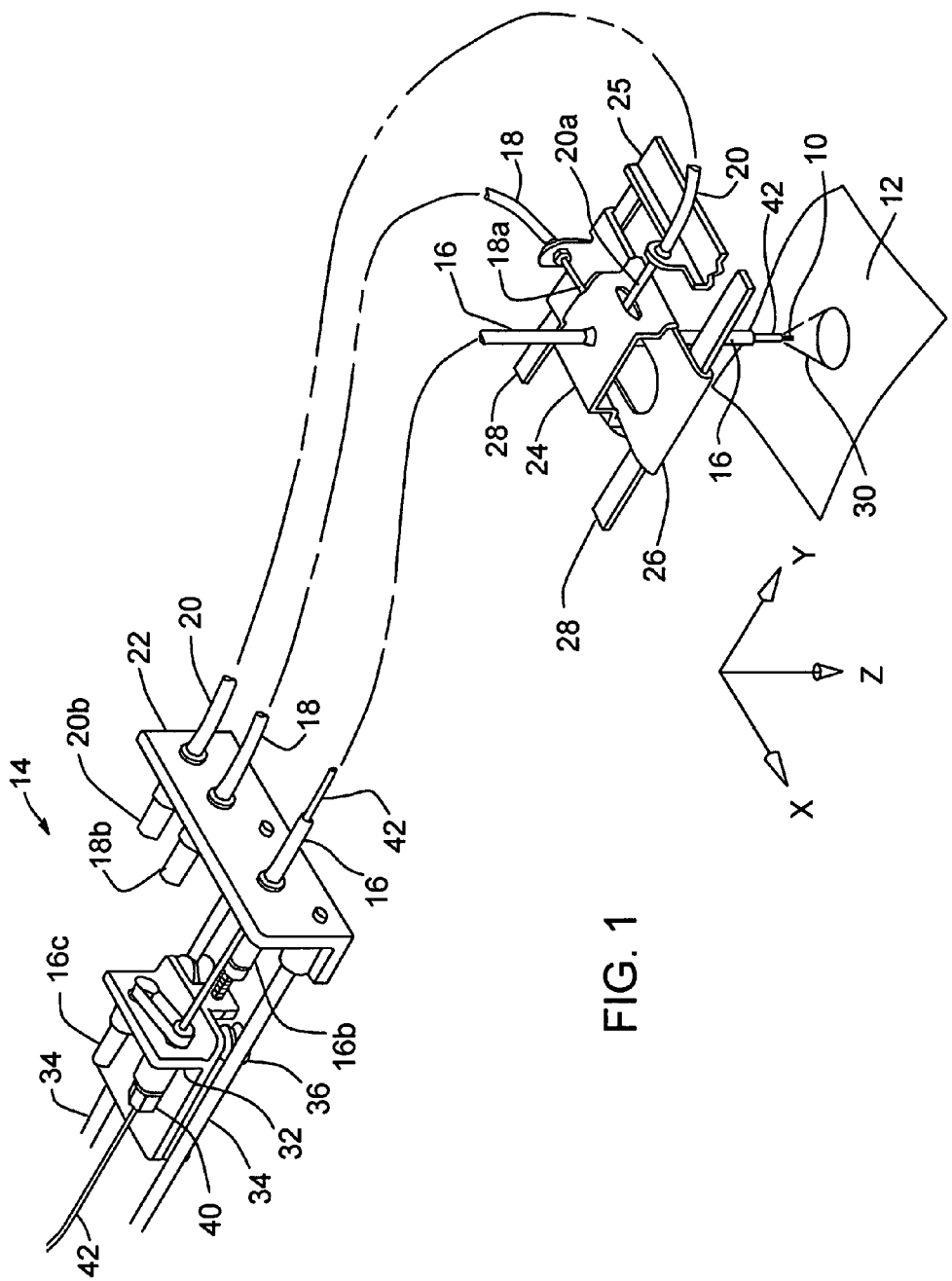
FIG. 1 is a schematic perspective view of an X, Y, Z embodiment of the invention positioned over a tissue surface to be treated.

Each case where radiotherapy of a surface area is indicated first involves planning. The area to be treated needs to be identified, and a prescription specified by a radiation oncologist. The prescription may involve local dose variations depending on the uniformity of the disease, its progression or extent as presented.

Planning also requires characterization of the source to be used, measured so as to include any attenuating effects from collateral apparatus which will be positioned within the emission pattern during the treatment to be performed. This characterization information is fed into the planning program for use in development of the treatment plan which in turn will later be used in establishing apparatus control parameters for the therapy.

With a prescription established and the source properly characterized and with both input into the treatment planning system, determination of a rastering treatment protocol, including proper control of apparatus parameters, can proceed. The physicist has the option of limiting rastering protocol passes to stop at the target area boundary as identified in the prescription, or of treating a regular shape, for example a square that circumscribes the target area, and masking the regions beyond the target area. Such a mask can be a lead sheet for example, with a cut-out area conforming to the treatment area and positioned appropriately on the patient. An alternate to lead sheet is a Flexishield® drape trimmed similarly to the lead, and similarly positioned. Flexishield elements are marketed by Xoft, Inc., the assignee of this application (see co-pending U.S. patent application Ser. No. 12/284,289). With either lead or Flexishield masks, markings can be used to indicate anatomical or other landmarks having to do with treatment delivery, as desired, and the masks can be placed either above or below a contact sheet, if one is used.

Any of several approaches to treatment plan creation may be used, depending in part on the skill of the radiation physicist or similar person developing the plan. A skilled physicist can often suggest a starting point for the apparatus and rastering parameters likely to be close to satisfactory. The planning software can then provide a comparison between the prescription and the trial plan. The modeling basis for comparison to the prescription is the cumulation of radiation emitted from all dwell points of the rastering protocol within a relevant range. Manual corrections can then be tried to iterate to a satisfactory plan within tolerable limits. If necessary, however, computational optimization through repeated permutations of apparatus parameters can be used to provide a satisfactory result. This data is then input to the control computer in compatible computer terms for source and servomotor control.

If desired, the plan can physically be verified for conformance to prescription by positioning, fixing and manipulating the apparatus to plan using an actual radiation source and radiochromic film (International Specialty Products, Wayne, N.J.). Verification can also be carried out using a surrogate and sensor for the radiation source. Such surrogate apparatus can be a visible light source and sensor, for example (such a light surrogate would of course be useful in creating a plan if virtual plan generation is not available in the planning program). Details of this and other surrogates will occur to and be well known by those of skill in the art.

Rastering protocols may be step-wise sequential as described above, or may be continuous, and any of many pathway patterns may be used—serpentine, spiral, parallel path but unidirectional, irregular, or others. Any pattern which is easily programmed during treatment planning is a likely candidate. If the source motion is continuous, absorbed radiation exposure must be determined by integrating target area segments proximate the rastering pathway.

Unlike surface treatment with prior art applicators, the therapist is free to select the pathway spacing such that almost any degree of uniformity can be achieved, or if appropriate, irregular spacing can be selected when the prescription suggests that would be an advantage. As stated above, however, there is little point in choosing finer divisions than those necessary to produce a satisfactory result within tolerable therapeutic limits.

A first apparatus embodiment of the invention is shown in FIG. 1. FIG. 1 depicts schematically, apparatus suitable for mechanically rastering a radiation source in a controlled manner over a tissue surface 12 to be treated using an X, Y, Z system of coordinates, as shown in the figure. A conventional servo module 14 is used to control X, Y and Z source (or source catheter) positioning in response to computer commands (the computer system is not shown). A source catheter sheath 16 (Z direction), an X direction sheath 18 and a Y direction sheath 20 are shown. The Z sheath has a fixed length between the control module base 22 and the X slide 24, and the Y sheath 20 having a fixed length between the control module base 22 and a bracket 25 secured to a rail 28. The X sheath 18 has a fixed length between the control module base 22 and the Y slide 26. Although the sheaths are advantageously flexible, it is also advantageous if the catheter sheath 16 is rigid below its point of attachment to the X slide 24 such that the source 10 in its catheter can be accurately positioned without flexure of the sheath 16.

The sheaths 18 and 20, with each of their manipulation cables or wires 18a and 20a respectively inside are, in effect, X, Y Bowden wires. The Y slide 26 is mounted on rails 28 (fixed to the bracket 25) and is translated by a wire 20a when driven by a servomotor 20b. The attachment of the wire 20a to the Y slide 26 is hidden under the slide 24 and not explicitly shown. The X slide 24 is mounted on the Y slide 26, and translated by a wire 18a when driven by a servomotor 18b. The attachment of the wire 18a to the X slide 24 is also not shown explicitly. The range of travel of the X and Y slides is preferably at least as great as that necessary to allow the source 10 to travel as required to properly treat the desired tissue area, thus eliminating need to reposition the apparatus to complete treatment. The rails 28 (and bracket 25) are secured to the operative table, bed, frame or other apparatus (not shown) upon which or adjacent to which the patient is positioned. As shown, an exemplary cone-shaped radiation beam 30 (collinear with source catheter 42) is shown impinging on the tissue surface 12. The radiation could be isotropic; if no, the cone of the beam preferably is wide, at least about 120° and probably at least about 180°, or even wider. The control module base 22 is stationary and may be mounted as convenient. Axial servomotors 18b and 20b (Baldor Electric Co., Fort Smith, Ark.) control X and Y positions of the source 10 respectively as stated above. A stage 32 is mounted rigidly on a pair of parallel bars 34. The stage comprises rollers 36 which allow the stage one degree of freedom along the bars, controlled by an axial servomotor 16b. A chuck 40 secures a source catheter 42 to the stage 32, so that movement of the stage relative to the base 22 effects Z direction movement of the source catheter 42. Preferably, the source 10 is in a fixed longitudinal position relative to the catheter 42.

It is well known that miniature x-ray sources alone, or in combination with their applicators, may be designed to emit substantially isotropically, through an arbitrary, restricted solid angle, or in other patterns as desired. This is generally accomplished by shaping or spacing their components, and/or by incorporating shielding elements into their designs (see, as examples, the Turner reference above, and co-pending U.S. patent application Ser. No. 12/075,120). Therefore, it is clear that the source 10 may be designed to project a solid angle radiation beam (not shown) at an angle to the axis of the source catheter 42, rather than collinearly as shown in FIG. 1. When such an angular source is employed, a rotational servomotor 16c (Baldor Electric Co.) may be used to control the azimuthal direction in which the solid angle is aimed.

Often, electronic sources are powered by a high-voltage electrical cable, and since the sources generate heat, the apparatus usually comprises provision for liquid or other cooling. U.S. Pat. No. 7,127,033 describes such cooling and is incorporated herein by reference in its entirety. A source catheter 42 as is depicted in FIG. 1 is commonly used to contain the source and high-voltage cable, as well as to manage the cooling medium. Such a catheter also generally fixes the source axially with respect to the end of the catheter such that the emission spectra are constant, at least with respect to any attenuation characteristics of the catheter itself.

If the catheter 42 (hence the source) is to protrude beyond the end of the catheter sheath below the X slide 24 as shown in FIG. 1, it is advantageous that the catheter portion near the end of and beyond the sheath be rigid so as to accurately position the source 10.

From well-known radiation decay characteristics and the desire to avoid overly intense radiation at the tissue surfaces, it is generally desirable that the source be spaced away from the treatment surface, as stated above. Where the tissue surface to be treated is non-planar, or at least sufficiently irregular in contour as to require source manipulation in the Z direction, any of several methods may be employed, some requiring mechanical contact to physically raise or drop the source, others using non-contact methods and still others a combination, examples of these being described below.

It may be undesirable to have the apparatus bear directly against the tissue being treated, if for no other reason than sterility. If so, the treatment area can be draped, or even mechanically protected by a rigid (aluminum is an example) or semi-rigid (silicone or polytetrafluorethylene are examples) sheet (see FIG. 2D) conforming to the tissue 12. (TEFLON is a polytetrafluorethylene material available from E. I. du Pont de Nemours, Wilmington, Del.) Where rigid, the sheet can be pre-contoured, and even used to urge the tissue into conformity with the sheet, whether planar or pre-shaped. Such an approach would be useful where a series of standard contour sheet shapes might be provided in a kit for recurrent situations. For the semi-rigid case, the main purpose would be to avoid scuffing the tissue as a mechanical probe slides over the surface of the treatment area. As stated above, the sheets can also be used to provide sterility on the patient side, and protection from contamination from the treatment apparatus, if by no other means than a conventional cloth drape. Where such a sheet is used, its attenuation characteristics must of course be incorporated into the treatment planning process, and equally, its beam hardening characteristics may be used to advantage. Aluminum and TEFLON are particularly useful in this regard. Where it would be useful to have the sheet provide proportional attenuation to simplify the treatment planning process, a sheet comprising silver film is useful (see co-pending U.S. patent application Ser. No. 12/072,620). Similarly, where fluorescence would assist therapy, the sheet can comprise phosphors which fluoresce when excited by x-rays. See, for example, U.S. Pat. No. 4,037,110, or Phosphor Technology, Ltd., Stevenage, United Kingdom.

Z control in non-planar treatment cases can be active or passive. A simple example for obtaining sufficient information for active Z control is through use of a surrogate in the catheter sheath to bear against the tissue to be treated (optionally covered by a conforming sheet or drape), such that when processed through the X,Y rastering protocol, Z information is obtained either mechanically, electrically or optically, defining the Z variations with respect to the X,Y positions throughout the treatment area. With Z definition, treatment planning can proceed with regard to X,Y positioning wherein the catheter and source are manipulated up or down (or perhaps rotationally where an angularly directed source is used) and kept at the desired range or distance from the tissue being treated.

Another option is shown in FIG. 2A. It comprises using a rounded, closed end 16a on the catheter sheath 16 which end extends beyond the source catheter 42 and hence the source 10, at the desired distance by which the source is to be removed from the treatment surface tissue 12 (or drape/sheet). The catheter sheath 16 is of a rigid engineering plastic, for example polycarbonate (among others, from Lonestar Chemical, Grapevine, Tex.). Although this catheter sheath might serve as the surrogate mentioned above for use during the planning process, the rounded sheath end can be used during treatment by mechanically holding the source away from the drape/sheet the desired distance. In this case, rather than being fixedly secured to the X slide 24, the sheath would have a sliding fit passing through the X slide, and if gravity alone is insufficient to maintain contact between the sheath and tissue (or drape/sheet), it could be spring biased into contact, or so biased by other conventional methods. Source characterization would need to take any attenuation characteristics of the extended sheath into account.

A still further Z control option is depicted in FIG. 2B and comprises use of an LVDT (linear variable differential transformer) 44, preferably with its probe 46 near the center of the emitted radiation incident on the tissue, and bearing against the sheet or tissue. Preferably, the attenuation effects of the probe are minimal. The LVDT is conveniently secured to the end of the sheath 16 by a bracket 48. Such apparatus can be used for characterizing tissue contours as part of the planning process such that the Z direction information is gathered and incorporated into the treatment plan.

Alternatively, the signals from the LVDT can be used in real time to control the Z manipulation of the source and source catheter (or for verification of treatment delivered by confirming source distance was adjusted as needed). If used in this manner, a nearly radiation transparent probe 46 is preferred, and its attenuation effects must be incorporated into the source characterization process.

A still further option to obtain Z direction control is by use of infra-red ranging as shown in FIG. 2C. With this method, a ranging device 50 (Acroname, Inc., Boulder, Colo.) is secured to the sheath 16 and its focus directed to the center of the emitted radiation as it impinges on the tissue 12. This is a non-contact method and the IR beam 52 projected onto the tissue is reflected back to the device 50 and the angles are sensed and used to accurately determine the range of the device from the tissue 12. This information can then be used through the computer to drive manipulation of the source catheter 42 or end member (and source) such that the tissue range of the source from the tissue is properly maintained during treatment. The information can be gathered in the planning process and incorporated in the treatment plan, or it can operate in real time for control purposes, or again for treatment verification via distance confirmation.

Figure 2D:
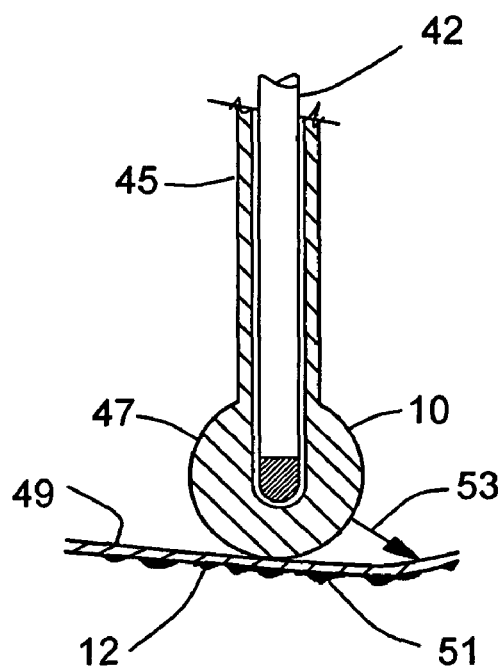

Yet another, and a preferred method of Z control incorporating physical contact between the catheter guide and the target tissue or an overlying sheet is shown in FIG. 2D. Prior art teachings of surface treatment by contact radiation applicators teach using the contact surface to urge the target tissue into conformance with the applicator surface (see Evans et al; International Journal of Radiation Oncology Biol. Phys. Vol. 39, No. 3, pp. 769-774, 1997, or U.S. Pat. No. 6,285,735). We have discovered unexpectedly, that purposely creating an air gap 53 laterally around a minimal contact point between the catheter sheath and the target tissue (or an overlying sheet in conformance to the target tissue) increases the dose contribution to adjacent areas surrounding each dwell point (and would do similarly if rastering were continuous). This occurs because the attenuation in the air gap 53 is substantially lower than that through tissue, or through a tissue surrogate like water. Because these lateral contributions accumulate from all adjacent dwell points, the lateral total is greater than expected, even though some are at low angles to the surface, and dwell points can by moved farther apart without degrading treatment uniformity, or alternatively, dwell times can be reduced since absorbed dose cumulates more rapidly. This in turn increases efficiency by reducing treatment time.

In instances of non-contact Z control, a non-spherical source guide tip shape can be used to enhance other system attributes as stated above. For example, if greater lateral dose intensity is desired, the tip can be configured accordingly, to enhance the size of the air gap.

In FIG. 2D, the catheter sheath 45 has a generally or substantially spherical tip 47, preferably of solid material, with the source 10 mounted on the source catheter 42, and preferably positioned such that the source is centered within the sphere. As in FIG. 2A, the sheath 45 is fixed relative to the source. The source could be in a different position in the sphere if desired. The spherical tip 47 bears against the target tissue 12, or in this case, against a conformal sheet 49 covering the tissue. Preferably, the spherical tip has a radius in the range of from 0.5 cm to 2 cm, or more preferably, about 1 cm. To the extent there are minor surface imperfections or variations in the target tissue, and if it is desired not to have voids underneath the sheet 49, a hydrogel 51, for example K-Y jelly (Johnson & Johnson, Cincinnati, Ohio) may be spread under the sheet 49. Note that the embodiment of FIG. 2A functions to some extent similarly to that of FIG. 2D, in that radiation is directed outwardly as well as directly under the applicator, increasing dose around the applicator tip and decreasing treatment time. The primary difference is that in FIG. 2A source is not surrounded by a material of selected attenuating (or hardening) properties at substantially constant radius around the source. The angular transmission of the radiation through the sheath 16 in FIG. 2A has some effect on beam distribution, since the depth of sheath material penetrated by the radiation varies with angle.

Figure 2E:
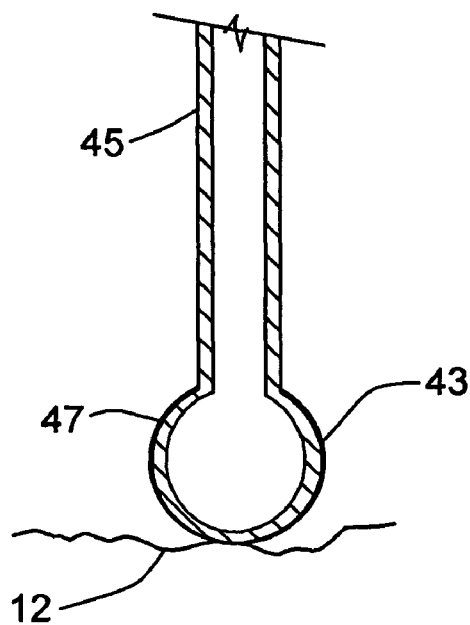

FIG. 2E shows a variation in the embodiment of FIG. 2D, wherein the spherical tip 47 of the catheter sheath 45 has a filtering layer 43 on its surface for purposes of hardening. This layer can be aluminum, TEFLON or silver in accordance with the teachings above. Contact with the target tissue 12 can be direct as shown (imperfections evident). The air gap is still formed, and the same benefits accrue.

If direct contact results in undesirable tissue "drag" during translation, several remedies are available. A coating of K-Y jelly on the tissue is one, a "hopping" motion between dwell points another. A further option is use of a conductivity gel (for example Spectra 360; Parker Laboratories, Inc., Fairfield, N.J.) under active Z control where a coating is applied, and the controller seeks to maintain contact using, for example, electrical make/break proximity with the tissue, or by sensing changes in capacitance between the catheter sheath and the coating.

Figure 3:
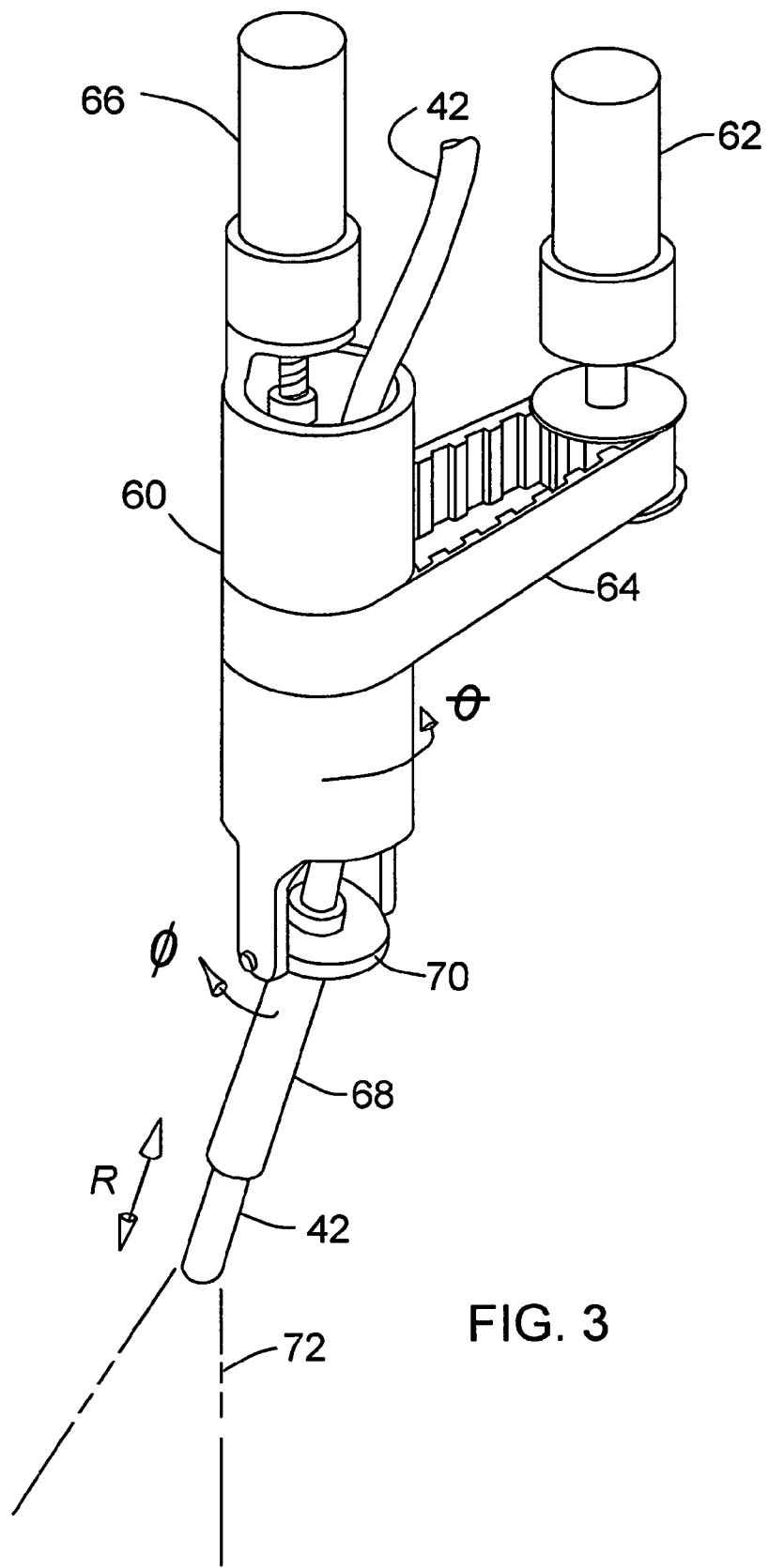
FIG. 3 is a schematic perspective view of an R, θ, Φ embodiment of the invention positioned over a tissue surface to be treated.
Figure 4:
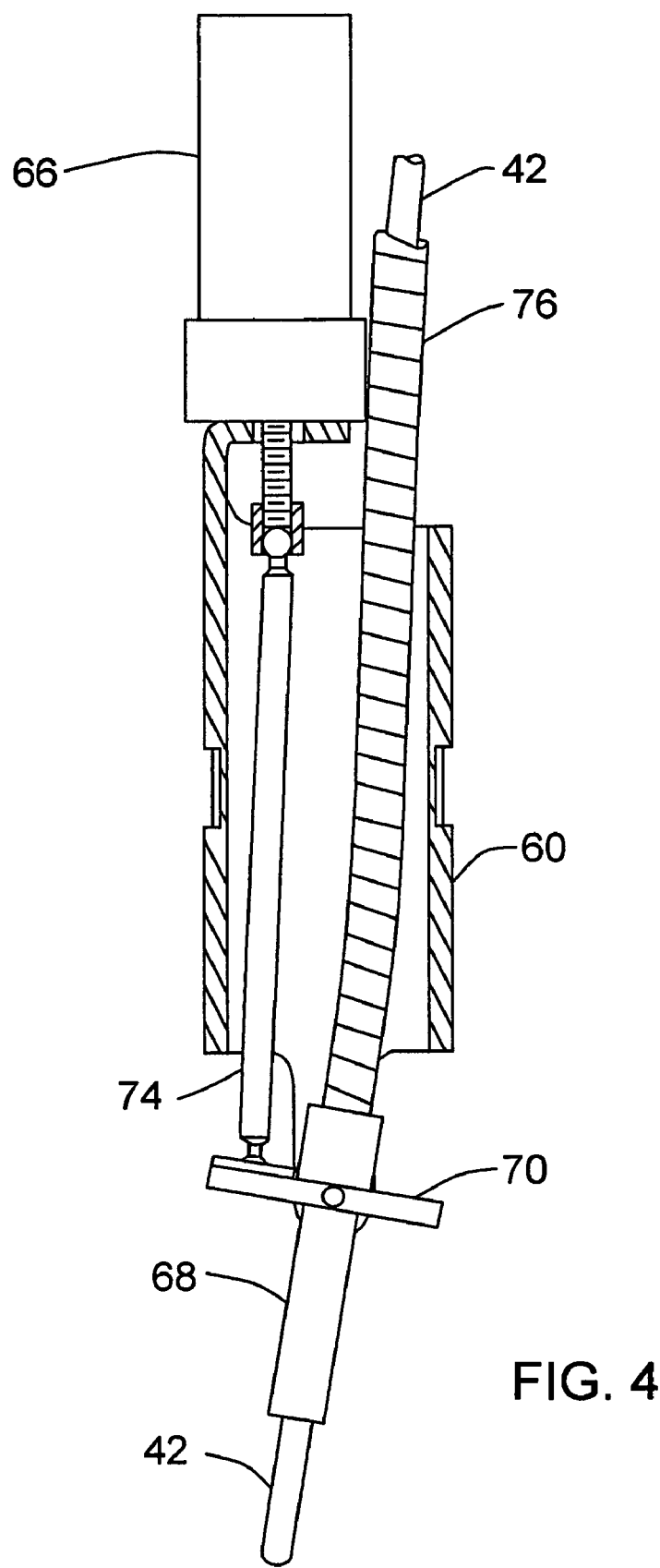

The discussion above largely pertains to an X, Y, Z coordinate system for scanning and control of treatment. An alternate coordinate system would be a polar or R, θ, Φ system ® being somewhat different from the radius R in planar polar coordinates). FIG. 3 shows such an apparatus schematically. A tube 60 is mounted in bearings securing the tube to a frame (neither shown) mounted on the operative table or bed. A servomotor 62 controls θ rotation (about a vertical axis) through a belt 64. A linear servomotor 66 controls Φ rotation (tilt or swing of end member 42 from vertical) as shown in FIG. 4 and as described in greater detail below. A rigid sleeve 68 secured centrally to a trunion mounted, washer-like disc 70 directs the source catheter (and source) toward the tissue to be treated. The vertical axis of θ rotation passes through the center of the axis of swing rotation Φ of the disc 70. The source catheter or end member 42 passes through the tube 60 in order to enter the sleeve 68, which in turn also passes through the center of the disc 70. Thus the center of the disc 70 comprises the center point about which both θ and Φ rotations occur, and through which the source is directed toward the tissue. The source (not shown) within the source catheter 42 emits radiation 72, which approaches the surface usually obliquely in this type of scanning. The range R between the source and the tissue being treated can be controlled by advancing the source catheter (and source) through the sleeve 68 passively or actively, but preferably by use of a servomotor element similar to that depicted in FIG. 1. (See the description of the servo module 14 described above for a servomotors reference.) If necessary to accommodate flexibility of the source catheter, the sleeve 68 may have an upward, flexible extension 76 (similar to elements 16, 18 or 20 as described in connection with FIG. 1 and shown in FIG. 4) connected to the control module base 22 of the servo module 14, thus forming Bowden wire type control as previously described.

FIG. 4 is a longitudinal section through the apparatus of FIG. 3 showing a connecting rod 74 with spherical ends joining the linear servomotor 66 to the disc 70 for Φ control, and also showing the optional, flexible sleeve extension 76. With such an arrangement, it is preferred that the tip of source catheter 42 be rigid for a sufficient length such that catheter deflection beyond the lower end of sleeve 68 is minimized during treatment.

Ranging methods described in connection with the discussion of FIGS. 2A-E can be used similarly with the apparatus of FIGS. 3 and 4 to map contours of the tissue to be treated, or to control the treatment itself as previously described.

If desired the Z direction control, or the X,Y,Z control described above (FIG. 1), can be combined with the R, θ, Φ control. The position of the center of the disc 70 (FIGS. 3 and 4) can be raised and lowered, and moved in X and Y directions as well, for repositioning as needed to treat the area or areas of target tissue.

The apparatus of both FIGS. 1 and 3 are shown schematically. Actual embodiments can vary in detail both as to construction as well as to the degrees of freedom through which the source may be manipulated, and are still to be included within the scope of the invention. As mentioned previously, although control of the apparatus parameters is discussed herein in terms of discrete, electromechanical actuators, robotics (for example, a robotic arm having appropriate degrees of freedom and control) can be used to replace those sorts of manipulators and control elements. Equally, the scale of the apparatus can be varied from that suitable for over-the-patient, extracorporeal treatment delivery or in miniaturized forms for use in conjunction with minimally invasive surgery. These forms also are to be included within the scope of the invention.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

We claim:

1. A method for treating a surface of living tissue of a patient, comprising:
   selecting an applicator for irradiating the tissue surface, the applicator including a source for emitting a beam of ionizing radiation,
   the applicator having a means for translating the beam from the source over a selected area of tissue so as to direct radiation as desired over the area to be treated, and the translating means being connected to a controller programmed with a treatment plan so as to cause the translating means to carry out a desired irradiation treatment,
   securing the applicator to a frame so as to retain the applicator at a desired position in relation to and distance from the patient tissue to be irradiated,
   prior to commencing irradiation, inputting to the controller the area of tissue to be treated, and
   with the controller and as directed by the treatment plan, activating the ionizing radiation source and the translating means to effect scanning the beam from the ionizing source over the area of tissue to be irradiated until essentially a prescribed dose has been delivered over the area of tissue.

2. The method of claim 1, further including moving the source in a Z or depth direction during scanning, under control of the controller, in accordance with measurements of depth from the applicator.

3. The method of claim 1, wherein the applicator includes a contacting probe, fixed relative to the source and extending toward the tissue from the source, and including engaging and sweeping the contacting probe against the patient's tissue or a protective sheet covering the tissue as scanning proceeds, following contours of non-planar tissue and moving the source in a Z or depth direction to follow the contours.

4. The method of claim 1, wherein the step of inputting the area of tissue to be treated includes placing the beam translating means to multiple positions that define the boundaries of the area prior to commencing irradiation, thus recording the positions in the controller.

5. The method of claim 1, wherein the step of scanning the beam comprises scanning the beam in a spiral pattern over the selected area of tissue.

6. The method of claim 1, wherein the step of scanning the beam including scanning the beam in a serpentine pattern over the selected area of tissue.

7. The method of claim 1, wherein the step of scanning the beam comprises scanning the beam in a parallel, unidirectional pattern over the selected area of tissue.

8. The method of claim 1, wherein the step of scanning the beam comprises tracing a movable element holding the source over a protective sheet which lies on the tissue.

9. The method of claim 1, further including, during scanning of the beam, controlling depth of a movable element holding the source relative to the area of tissue during scanning of the beam over the selected area of tissue.

10. The method of claim 9, wherein the applicator includes a depth measurement system connected to the controller and the method including determining distance of tissue from the source using the depth measurement system during scanning, and controlling the beam in accordance with determined distance.

11. The method of claim 1, wherein the source of ionizing radiation comprises an electronic controllable x-ray source controllable as to intensity and energy of radiation, and including controlling intensity and energy of the radiation beam during scanning, in accordance with the treatment plan programmed into the controller.

12. The method of claim 1, wherein the scanning of the beam includes X-Y control of beam position within a plane, and further includes Z or depth control.

13. The method of claim 1, wherein the applicator includes a generally spherical applicator tip surrounding the source, and the applicator substantially not restricting radiation in lateral directions from the source, and the method including engaging and sweeping the applicator tip against the patient's tissue or a protective sheet covering the tissue as scanning proceeds, so that radiation is directed laterally, outwardly and obliquely from the applicator tip as well as directly in line with the applicator's orientation, such radiation passing through an air gap where the radiation is substantially unattenuated, providing a greater accumulated radiation dose from scanning of the applicator.

14. The method of claim 13, wherein the generally spherical tip comprises a solid body surrounding the source.

15. The method of claim 14, wherein the generally spherical tip has different beam attenuating characteristics in different directions from the source, providing a non-uniform distribution of radiation for different directions as scanning proceeds.

16. The method of claim 14, wherein the generally spherical tip has a radius of about 0.5 to 2 cm.

17. The method of claim 1, wherein the scanning of the beam comprises manipulating an end member holding the source as to tilt from vertical and as to rotation about a vertical axis, thus including directing the beam obliquely toward the surface during scanning.

18. The method of claim 17, wherein the scanning of the beam further includes range adjustment by which the end member with the source is moved on a longitudinal axis of the end member toward or away from an axis of tilt of the end member.

19. The method of claim 18, wherein the end member is contained coaxially and slidably within a sleeve and is controlled by a mechanical manipulator via a sheath-encased wire.

20. The method of claim 1, wherein the step of scanning the beam includes manipulating the source using a mechanical manipulator connected to movable sliding elements of the applicator, secured to an end member containing the source, and the sliding elements being connected to the mechanical manipulator by control wires slidable within sheaths.

* * * * *